US005660865A

United States Patent [19]
Pedersen et al.

[11] Patent Number: 5,660,865
[45] Date of Patent: Aug. 26, 1997

[54] SURFACE TREATMENT COMPOSITION

[75] Inventors: Arne Pedersen, Hinnerup; Frank Johannsen, Viby J, both of Denmark

[73] Assignee: Aarhus Oliefabrik A/S, Aarhus, Denmark

[21] Appl. No.: 406,942

[22] PCT Filed: Sep. 24, 1993

[86] PCT No.: PCT/DK93/00308

§ 371 Date: May 8, 1995

§ 102(e) Date: May 8, 1995

[87] PCT Pub. No.: WO94/07373

PCT Pub. Date: Apr. 14, 1994

[30] Foreign Application Priority Data

Sep. 24, 1993 [DK] Denmark .................. 1190 92

[51] Int. Cl.$^6$ .................................. A23D 9/007
[52] U.S. Cl. .................... 426/99; 426/307; 426/601
[58] Field of Search .................. 426/99, 306, 307, 426/601

[56] References Cited

U.S. PATENT DOCUMENTS

| | | | |
|---|---|---|---|
| 2,640,040 | 5/1953 | Lehman | 426/307 |
| 3,338,720 | 8/1967 | Pichel | 99/123 |
| 3,397,997 | 8/1968 | Japikse | 99/118 |
| 3,526,515 | 9/1970 | Werben | 426/306 |
| 3,734,748 | 5/1973 | Ueno | 426/307 |
| 3,867,556 | 2/1975 | Darragh | 426/99 |
| 3,876,699 | 4/1975 | Miyano | 426/99 |
| 4,207,347 | 6/1980 | D'Atri | 426/307 |
| 4,704,288 | 11/1987 | Tsau | 426/99 |
| 4,753,807 | 6/1988 | Fuseya | 426/99 |
| 4,839,184 | 6/1989 | Cherukure | 426/99 |
| 4,871,558 | 10/1989 | Tackikawa | 426/99 |
| 4,880,646 | 11/1989 | Lew | 426/307 |
| 4,885,175 | 12/1989 | Zebell | 426/99 |
| 4,946,694 | 8/1990 | Gunnerson | 426/273 |
| 5,147,676 | 9/1992 | Talbot | 426/601 |
| 5,215,780 | 6/1993 | Meridenbauer | 426/306 |
| 5,380,538 | 1/1995 | Wheeler | 426/99 |
| 5,391,383 | 2/1995 | Sullivan | 426/99 |
| 5,468,507 | 11/1995 | Czap | 426/99 |

FOREIGN PATENT DOCUMENTS

| | | |
|---|---|---|
| 3011881 | 10/1981 | Germany . |
| 2832636 | 1/1986 | Germany . |
| 60-221035 | 11/1985 | Japan . |
| 399648 | 10/1933 | United Kingdom . |
| 2204590 | 11/1988 | United Kingdom . |

OTHER PUBLICATIONS

Jamieson 1943 Vegetable Fats and Oils, American Chemical Society Monograph Series Reinhold Publishing Corp. NY pp. 88–89.

Primary Examiner—Carolyn Paden
Attorney, Agent, or Firm—Michael L. Dunn

[57] ABSTRACT

A composition for use as a substitute for petrolatum and for surface treatment of confectionery, food products and surfaces which get in contact therewith as well as for external treatment of animals and plants comprises (a) oxidation resistant glyceride oil and/or liquid wax, (b) solid wax, which may be omitted if (a) comprises liquid wax, (c) structuring fat, and optionally (d) additions selected from crystallization inhibitors, hydrolysis inhibitors, food product ingredients, additives to food products, diet supplements, bioactive substances, cosmetic ingredients, pigments, and solvents. The combination of oxidation resistant glyceride oil, wax and structuring fat provides a composition with a semi-transparent, petrolatum-like structure having a high taste and smell stability, good gloss and anti-sticking effect, regulated adhesion and a very fine crystal structure. The composition is biocompatible by topical and oral administration and may advantageously be used instead of petrolatum and mineral oil based surface treatment compositions.

34 Claims, 4 Drawing Sheets

SURFACE TREATMENT COMPOSITION

This invention concerns a composition for use as a substitute for petrolatum and for surface treatment of confectionery, food products and surfaces which get in contact therewith, as well as for external treatment of animals and plants.

BACKGROUND OF THE INVENTION

Petrolatum Vaseline has been used for years in cosmetics and pharmacy for i.a. ointments and emulsions, because of the oil-binding, consistency-imparting and skin-refatting properties of the substance, which has also been used as a vehicle for skin active components.

Further, for many years it has been known to use surface treatment compositions in the manufacture of confectionery (e.g. liquorice, wine gum/jelly articles) and dried fruit (e.g. raisins, prunes, nuts) to give the products a shiny and glossy surface, to reduce the tendency of desiccation of the product as well as to prevent the individual product articles from sticking together.

It is also known to use paraffin oil and/or petrolatum for treating surfaces which get in direct contact with food products or food product ingredients, e.g. in the meat and bakery industries.

Furthermore, it is known to use mineral oil based products as a vehicle for bioactive substances and the like for application to animals and plants either directly or in the form of an emulsion.

Petrolatum is a mixture of predominantly saturated, solid and liquid hydrocarbons recovered from residues from distillation of mineral oil. Typically, the hydrocarbons consist of 5–20% n-paraffins as well as branched and cyclic, however, rarely aromatic components. Owing to this hetorogeneous composition petrolatum has a characteristic soft, amorphous structure over a wide temperature range.

Paraffin oil which is a mineral oil fraction, has been used for surface treatment of liquorice and jelly articles (e.g. wine gum), and here wax and/or petrolatum is generally added to increase the adhesion, the gloss and in particular the anti-sticking effect.

Paraffin oil has likewise been used for surface treatment of dried fruit (e.g. raisins), primarily as a gloss agent and a preservative, but also as an anti-sticking agent for raisins for industrial purposes (e.g. used for dragees, etc.). Advantageously, a wax type, typically beeswax, may additionally be added to raisins used in muesli products.

In recent years several countries have focused on limiting the use of paraffin oil and other mineral oil products in food products, cosmetics and pharmaceuticals because of health reasons.

So-called MCT oils (Medium Chain Triglycerides) and oxidation resistant glyceride oils, so-called high stability oils, have been used as a substitute for paraffin oil in surface treatment compositions for food products.

MCT oils are synthetic triglycerides made from glycerol and predominantly caprylic, captic and lauric acid in varying quantitative proportions. They are supplied i.a. under the trade name "Crodamol GTCC" by Croda Surfactants Ltd., England; under the trade name "Miglyol 810" by Hüls AG, Marl, Germany; under the trade name "Neobee M-5" by Stepan Company Illinois U.S.A.; and under the trade name "Delios MCTs" by Henkel Corporation, USA.

For use in surface treatment compositions for food products the MCT oils have the following advantages:

Good oxidation stability.
Liquid at room temperature.
and i.a. the following drawbacks:
Low viscosity.
Labile to hydrolysis with consequent diverging aftertaste ("soap taste").
Aggressive to certain plastics materials.
May cause greasy appearance, because mixtures of MCT oils and wax types are milk white, with visible crystals, which may cause deposition of dim crystalline spots on clear packages.

Known oxidation resistant oils, which are extensively used for surface treatment of raisins, are partly liquid fractions of hardened vegetable liquid oils, (cottonseed oil, soybean oil, palm oil, rapeseed oil). They are supplied under the trade name "Durkex 500" by Loders & Croklaan, Holland; under the trade name "Akorex" by Karlshams Oils and Fats AB, Sweden; and under the trade name "Coatex 01" by Aarhus Oliefabrik A/S, Denmark.

For surface treatment of raisins these oxidation resistant oils have the following advantages:

Good stability to oxidation and hydrolysis.
Predominantly fluid at room temperature.
No short chain fatty acids which might give poor taste by hydrolysis.
and i.a. the following drawbacks:
The relatively high melting point may cause crystallization of fat on surface treated raisins, which may result in a dull tinge on the raisins.
Too poor adhesion, which, on surface treated raisins, may cause separation of oil and sticking together and desiccation of the raisins.

In particular, U.S. Pat. No. 4,946,694 discloses a multi-step process for coating sticky fruits, such as dates, figs, candied fruits and dried fruits wherein the fruit is coated with a first composition comprising a suspension of vegetable wax in vegetable oil, for example the above-mentioned "Durkex 500", in the presence of a wetting agent, and then a second composition comprising a solution of a protein in a suitable inert, volatile solvent is added to the fruit, following which the fruit is dried.

As far as is known, oxidation resistant oils have not been used for surface treatment of liquorice and wine gum.

Chemically, natural waxes are usually mixtures of esters of long chain fatty acids and long chain fatty alcohols having a varying content of free fatty acids and alcohols as well as hydrocarbons. Vegetable waxes comprise e.g. carnauba wax, candelilla wax, shellak, liquid jojoba oil and hardened jojoba oil. Animal waxes comprise e.g. beeswax, bleached beeswax (cera alba), wool wax (lanolin) and spermaceti. Synthetic waxes are usually mixtures of esters of long chain fatty acids and fatty alcohols. Such are supplied i.a. under the trade name "Beeswax Synthetic" by Frank B. Ross Company, Inc., New Jersey, USA; under the trade name "Synthetic Candelilla" by Koster Keunen Holland BV, Holland; and under the trade name "Cetiol J 600" (synthetic jojoba oil) by Henkel KGaA, Düsseldorf, Germany.

Thus, it is generally known to use the above-mentioned liquid and partly liquid oils and mixtures of these with waxes for surface treatment of confectionery and dried fruit.

On the other hand, it cannot be seen that it has been attempted to replace petrolatum for cosmetic and pharmaceutical use by a combination of such glyceride oils and waxes.

For other applications, e.g. nougat centers, chocolate sandwich spread and liquid margarine, it is generally known to use liquid oil and a so-called structuring fat (hardstock).

A structuring fat typically consists of mixtures of partly hardened and/or fully hardened fats, and/or high-melting fats or fractions thereof.

For example, U.S. Pat. No. 3,397,997 describes the use of a structuring fat (hardstock) in connection with the production of liquid shortenings. One example reports the use of a structuring fat in liquid glyceride oil in an amount of 5.40% (varying in the range 1–8% hardstock and 92–99% liquid triglyceride oil). The structuring fat consists of a mixture of hardened soybean oil having an iodine value of 8 and hardened erucic acid rich rapeseed oil having an iodine value of 8 in the ratio 3:2 (varying in the range 1:4–4:1). The two hardened fats exhibit differences in crystallization, the soy component being so-called α-crystallizing and the rape component being α'-crystallizing. U.S. Pat. No. 3,338,720 describes the use of 2.5% hardened cottonseed oil (melting point 58°–60° C.) as a structuring fat together with 97.5% liquid vegetable oil used as the fat phase in a liquid margarine which is cooled in a surface-scraped heat exchanger (tube cooler). DE Patent Specification No. 2 832 636 describes fat mixtures having a content of a triglyceride mixture on the basis of fatty acids having 8 and 10 carbon atoms, the weight ratio of fatty acids having. 8 carbon atoms to fatty acids having 10 carbon atoms being from 30:70 to 55:45, and an addition of 2–10% by weight of a hard fat component consisting of triglycerides of saturated fatty acids, the majority of which contains 12–24 carbon atoms, and having an iodine value not exceeding 2 for use in food products, in particular as a fat base in margarine.

It is also known that certain substances, such as e.g. partial glycerides, sorbitan fatty acid esters and lecithin, may be used as crystallization inhibiting additives in fat mixtures.

SUMMARY OF THE INVENTION

According to the invention it has surprisingly been found that the combination of:
  (a) oxidation resistant glyceride oil and/or liquid wax,
  (b) solid wax, which may be omitted, however, if (a) comprises liquid wax,
  (c) structuring fat, and optionally
  (d) additions selected from one or more of the following groups:
    crystallization inhibitors,
    hydrolysis inhibitors,
    food product ingredients,
    additives for food products,
    diet supplements,
    bioactive substances,
    cosmetic ingredients,
    pigments, and
    solvents provides a composition having the following properties:
  1. High taste and smell stability.
  2. Semitransparent, petrolatum-like consistency.
  3. Good gloss-giving effect.
  4. Good anti-sticking effect.
  5. Regulated adhesion preventing separation of the oil and ensuring even distribution of the composition on surfaces.
  6. Very fine crystal structure which does not deposit visible, dim spots on a clear retail package.
  7. Non-aggressive to plastics packages.
  8. Biocompatible by topical and oral administration and biologically degradable.
  9. Non-occlusive to the pores of the skin—a problem which has been advanced in connection with petrolatum.

The composition of the invention may be used in the same manner as petrolatum for cosmetic and pharmaceutical use. The composition may be used for skin care, partly alone, partly—and advantageously—in preparations which may be anhydrous (e.g. ointments) or in emulsion form.

The composition of the invention may also advantageously be used for surface treatment of confectionery and food products, such as fresh and dried fruit. The abovementioned properties make the composition suitable for this use, and in particular the regulated adhesion ensures an even distribution of the surface treatment composition on the articles, which prevents desiccation of the product. Furthermore, there is no separation of oil, which might be aesthetically unattractive to the consumers.

In the same manner as paraffin oil and petrolatum, the composition of the invention may be used for treatment of surfaces, including machine parts, which are in direct contact with food products or food product ingredients. For example, it may be used for surface treatment of so-called fast speed choppers in the meat industry in order to prevent rust attacks after cleaning, for treatment (lubrication) of movable mould parts in e.g. portioning equipment, for treatment of movable parts in meat chopping machines and for treatment of valve parts, gaskets and threads in equipment for the production of food products. The composition may also be used advantageously for surface treatment of e.g. stainless steel tables which are subjected to corrosive brine. The composition may advantageously be applied to e.g. rotating knives in connection with slicing of baked bread, where a thin film is left on the bread slices which i.a. reduces desiccation and facilitates separation of the individual slices ("blade fat"). The composition may also be used for application to baking tins and on conveyors ("baking belts") in industrial ovens. The composition may moreover be used for surface treatment of food product packages, where a release effect is desired between package and product, e.g. wrapping paper and cardboard boxes.

Furthermore, the composition of the invention may be used as a vehicle for bioactive substances, such as pesticides (e.g. insecticides, acaricides, vermicides, fungicides, herbicides) and insect-repelling substances for application on animals or plants. The bioactive substance is dissolved or suspended in the composition, and this is applied either directly or in the form of an emulsion. Direct application on animals takes place by the pour-on or spot-on methods, the composition, containing e.g. anthelmintics or insect-repelling substances, being applied locally on the animal, e.g. on the back. The bioactive substances either remain on the back of the animal or migrate through the skin. Application of the emulsion on animals takes place either by immersing the whole animal in a bath of an aqueous emulsion of the composition containing the bioactive substances, or by spraying the animal with a corresponding emulsion. This provides an even distribution of the composition on the body of the animal, which ensures a longer and more effective protection of the animal. Application on plants can suitably take place by spraying these with the composition containing the bioactive substances or with an emulsion thereof.

DETAILED DESCRIPTION OF THE INVENTION

Figure 1:
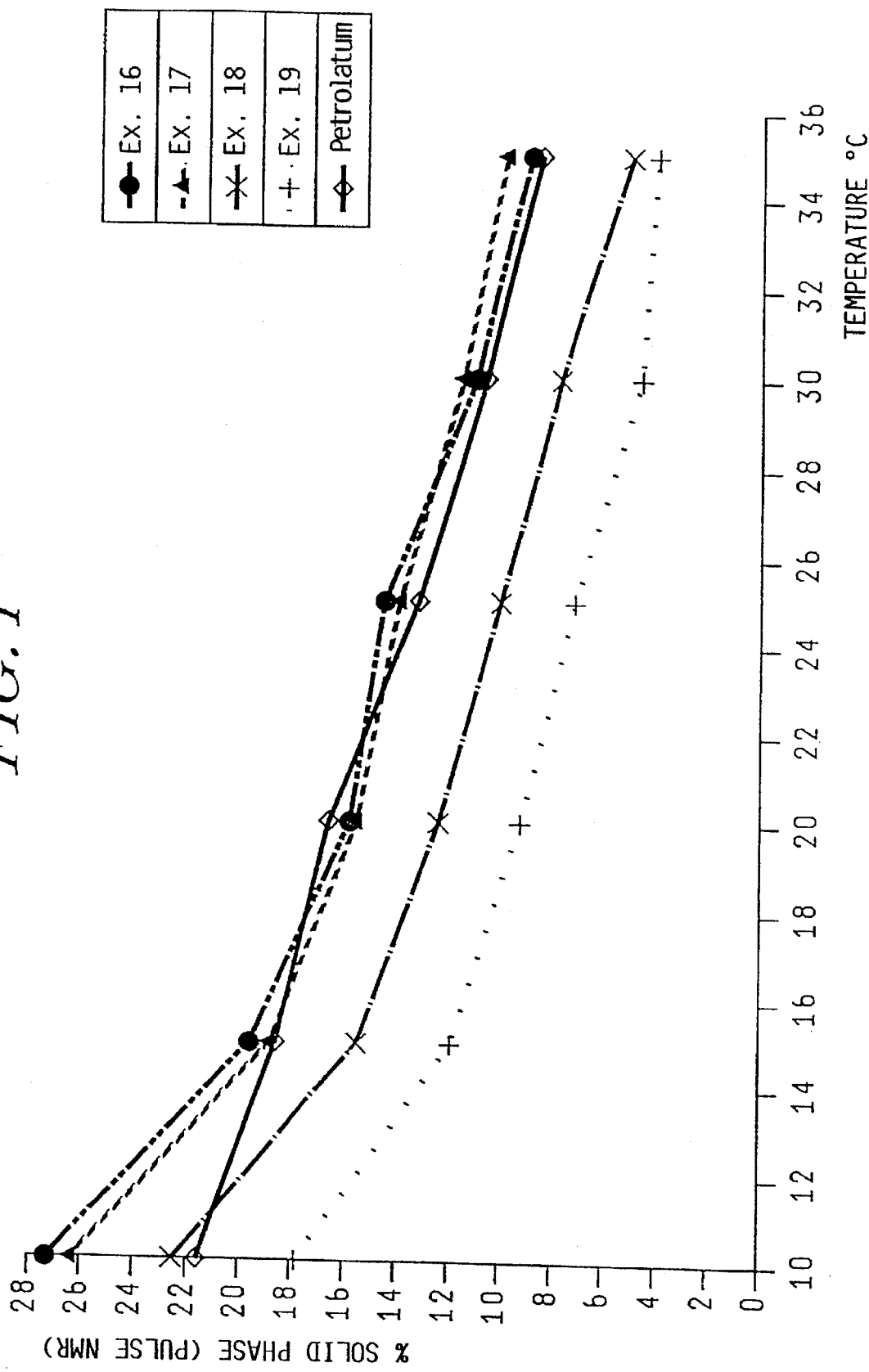
FIGS. 1, 2, 3 and 4 show the solid phase of the compositions 16–19, 20–23, 24–29 and 30–34 respectively as compared with the solid phase of a commercial petrolatum at various temperatures.

A composition according to the invention typically contains (a) 60–99.9% by weight of oxidation resistant glyceride oil and/or liquid wax, (b) 0–30% by weight of solid wax, (c) 0.1–20% by weight of structuring fat, (d) 0–20% by weight of additions selected from the groups stated in claim 1.

Embodiments of the composition of the invention which do not contain liquid wax typically contain (a) 60–99.8% by weight of oxidation resistant glyceride oil, (b) 0.1–30% by weight of solid wax, (c) 0.1–20% by weight of structuring fat, (d) 0–20% by weight of additions selected from the groups stated in claim 1.

More preferred embodiments of the composition of the invention contain (a) 70–99.7% by weight of oxidation resistant glyceride oil and/or liquid wax, (b) 0–20% by weight of solid wax, (c) 0.3–20% by weight of structuring fat, (d) 0–10% by weight of additions selected from the groups stated in claim 1.

Embodiments of the composition of the invention particularly useful for surface treatment of confectionery, food products and surfaces which get in contact therewith and for external treatment of animals and plants contain (a) 70–99.6% by weight, preferably 80–99.4% by weight of oxidation resistant glyceride oil and/or liquid wax, (b) 0.1–20% by weight, preferably 0.1–10% by weight, of solid wax, (c) 0.3–10% by weight, preferably 0.5–6% by weight, of structuring fat, (d) 0–10% by weight, preferably 0–5% by weight, of additions selected from the groups stated in claim 1.

Embodiments of the composition of the invention which are particularly useful as a replacement for petrolatum vaseline, contain (a) 60–87% by weight of oxidation resistant glyceride oil and/or liquid wax, (b) 3–10% by weight of solid wax, (c) 10–20% by weight of structuring fat, (d) 0–20% by weight of additions selected from the groups stated in claim 1.

For the purpose of this invention oxidation resistant glyceride oil means a predominantly liquid glyceride oil which does not develop unacceptable smell and taste within six months when expediently stored at room temperature.

The oxidation resistant glyceride oil in the composition of the invention may advantageously be oxidation resistant oils of vegetable origin selected from (1) at least partly liquid, optionally interesterified vegetable oils and fractions thereof (2) at least partly liquid fractions of optionally interesterified solid vegetable fats (e.g. palm oil), and (3) at least partly liquid fractions of hardened, Optionally interesterified vegetable oils or fat fractions, and these oils may optionally be admixed with antioxidants and/or hydrolysis inhibiting substances.

Suitable vegetable oils for producing the oxidation resistant glyceride oil incorporated in the composition of the invention can be recovered from plants belonging to the Palmae family and from plants belonging to one or more of the genera Garcinia, Pentadesma, Glycine, Carthamus, Olea, Brassica, Helianthus, Zea, Gossypium, Oryza, Shorea, Butyrospermum, Sesamum, Passiflora, Camelina, Limnanthes, Prunus, Triticum, Vitis, Arachis, Corylus, Persea, Madhuca, Juglans, Moringa, Macadamia, Papaver, Carica, Crambe, Adenanthera, Thevetia, Trigonella, Guisotia, Pinus, Hevea, Ricinodendron, Jatropha, Tamarindus, Theobroma, Simarouba, Oenothera, Borago, Cassinia, Flaveria, Stirlingia, Isotropis, Cuphea, Aleurites, Allanblackia, Trichodesma, Phylianthus, Vaterica, Melia, Alphictonia, Atalaya, Stylidium, Cyperus, Calophyllum, Aloe, Medicago, Mangifera, Curupira, Pongamia, Azadirachta, Myristica, Canarium, Ricinus, Cucurbita, Sapium, Cannabis, Ceiba, Bombax, Linum, Licania, Thea, Camellia, Vernonia and Virula. Particularly useful at least partly liquid vegetable oils are obtained e.g. from soy, rape, sunflower, corn, cottonseed, grape seed, thistle, sesame, groundnut and high-oleic acid containing hybrids of rape, sunflower, soy, thistle, groundnut and palm.

Such oxidation resistant oils of vegetable origin also comprise the previously mentioned high stability oils, whose defects in connection with surface treatment of dried fruit are remedied by the use in the composition of the invention.

Furthermore, animal fats may be used as an oxidation resistant glyceride oil, which, if necessary, have been made oxidation resistant by hardening and/or addition of antioxidants. Animal fats normally have poor stability to oxidation owing to a content of special multi-unsaturated fatty acids, e.g. arachidonic acid having 4 double bonds in lard, and lack of natural antioxidants. Such fats can obtain increased oxidation stability through a suitably slight hardening, following which more or less liquid fractions can be recovered by fractionation. Examples of useful animal oils include such at least partly liquid fractions of suitably hardened lard, tallow, butter fat or marine oils.

Also synthetic glycerides satifying the conditions of being oxidation resistant and of being at least partly liquid at room temperature (oils) may be used in the composition of the invention. Examples of such synthetic glyceride oils include di- and tri-esters of glycerol and fatty acids having 6–26 carbon atoms, predominantly mono-unsaturated fatty acids or slightly hardened multi-unsaturated fatty acids, as well as the previously mentioned MCT oils, whose defects in connection with surface treatment of confectionery and dried fruit can be remedied to some extent by use in the composition of the invention.

As mentioned, it is a requirement that the present glyceride oils have prolonged stability, and this typically means high stability to oxidation and hydrolysis.

In the course of time a large number of methods have been developed for evaluating the stability of oils/fats to oxidation. Most methods are so-called accelerated tests, i.e. the oxidation process is accelerated by performing measurements at a high temperature and optionally with air blow through or in an atmosphere of pure oxygen. The following methods may be mentioned:

The Schaal oven test in which the oxygen absorption is gravimetrically observed as a function of time.

The very widely used AOM (Active Oxygen Method) stability test in which 2.33 ml atmospheric air per second bubble through 20 ml of oil/fat at 97.8° C. The number of hours it takes the peroxide number in the loaded oil to reach the value 100 is called the AOM stability.

The test with the apparatus "Rancimat" (available from Methrom, Switzerland), is used much today, wherein a relative determination of the stability of a given fat to oxidation is automatically obtained. Like in the AOM test a specific amount of atmospheric air (normally 19 liters per hour) bubbles through a given test amount of oil/fat (normally 5.0 g) at a specific high temperature (typically in the range 100°–130° C.). At a certain time the components formed by the oxidation, conveyed by the bubbling air to a condensation chamber of distilled water, will give rise to an increase in the conductivity in this; and by automatic plotting of a curve of the conductivity as a function of time the stability can be determined as the elapsed time to the point of discontinuity of the curve (Rancimat time, measured in hours). This method is useful for the most common types of oils/fats, including MCT oils.

Finally, the test with the apparatus "Oxidograph" (available from Mikrolab, Denmark) should be mentioned, which is based on registration of the oxygen absorption as a function of time, measured manometrically by means of a pressure transducer system. Samples of 5.0 g oil/fat are placed in specially cleaned glass reactors (volume of 100 ml) with small bar magnets for stirring via rotating magnets in the heating block, which can operate six samples.

The heating system is activated to reach the desired measuring temperature.

The glass reactors and the adapters to the pressure transducer systems are flushed with pure oxygen for 30 seconds (2–3 liters of oxygen per minute) for removing the contained atmospheric air. The glass cylinders are placed in the heating block at time zero. After 15 minutes for establishing pressure equilibrium the adapters are connected to the pressure transducer systems. The changes in presure are registered in relation to the time. The Oxidograph times are determined as the elapsed time to the point of discontinuity of the curve.

The large surface With respect to the amount applied makes greater demands on the stability of the glyceride oil, and therefore selection of particularly oxidation resistant glyceride oils and/or addition of antioxidants is expedient.

The results of accelerated oxidation tests (e.g. rancimat time) cannot be correlated directly to stability conditions at room temperature, precisely because the measurement conditions are accelerated (increased temperature and frequently loading With atmospheric air or pure oxygen). But generally desirable Rancimat times (120° C.; 19 liters of air per hour) of oxidation resistant oils are over 3 hours, preferably over 5 hours, more preferably over 10 hours and most preferably over 30 hours.

Some typical oxidation resistant oils which may be used in the composition of the invention are shown in the following Table 1, with their melting points and Rancimat and Oxidograph times.

A general rule-of-thumb is that for each 10° C. increase in temperature the rate of oxidative deterioration is doubled (Journal of the American Oil Chemists Society, Vol. 69, 1992, pp. 525–527; and SOFW-Journal, 119. Jahrgang, 1993, pp. 520–533). In order to facilitate comparisons of the various oils the Rancimat and Oxidograph times stated in Table 1 are recalculated to 120° C. in the following Table 2.

TABLE 1

| Oil | Antioxidant | ppm | Measured Oxidograph time, h | Measured Rancimat time, h | Temp. °C. |
|---|---|---|---|---|---|
| Soybean oil having | None | | 7.8 | 14.8 | 100 |
| | Propyl gallate | 100 | 14.2 | 28.0 | 100 |
| | BHA | 100 | 8.1 | 15.3 | 100 |
| PV 0.8 | BHT | 100 | 8.8 | 15.8 | 100 |
| AV 3.7 | Ascorbyl palmitate | 200 | 8.4 | 20.8 | 100 |
| M.p. −23 to −20° C. | Mixed natural tocopherols | 200 | 7.4 | 15.0 | 100 |
| Rapeseed oil having | None | | 9.3 | 16.4 | 100 |
| | Propyl gallate | 100 | 18.2 | 30.2 | 100 |
| PV 0.2 | TBHQ | 100 | 18.4 | 38.3 | 100 |
| AV 3.7 | Ascorbyl palmitate | 200 | 10.5 | 27.0 | 100 |
| M.p. −5° C. | Mixed natural tocopherols | 200 | 9.3 | 15.5 | 100 |
| Corn oil having | None | | 12.8 | 24.2 | 100 |
| PV 0.0 | Propyl gallate | 100 | 21.4 | 36.8 | 100 |
| AV 14.1 | TBHQ | 100 | 19.7 | 39.5 | 100 |
| M.p. −18 to −10° C. | Mixed natural tocopherols | 200 | 13.0 | 24.2 | 100 |
| Sunflower oil of a high oleic acid | None | | 4.1 | 5.9 | 120 |
| content having | Propyl gallate | 100 | 5.7 | 8.9 | 120 |
| PV 3.1 | TBHQ | 100 | 6.1 | 10.2 | 120 |
| AV 21.7 | BHA | 100 | 5.9 | 6.7 | 120 |
| M.p. 7° C. | Mixed natural tocopherols | 200 | 5.7 | 8.7 | 120 |
| Double fractionated palm oil having | None | | 7.2 | 12.7 | 120 |
| PV 0.1 | Propyl gallate | 100 | 11.1 | 18.8 | 120 |
| AV 8.7 | TBHQ | 100 | 9.3 | 18.5 | 120 |
| M.p. approx. 16° C. | Mixed natural tocopherols | 200 | 7.4 | 13.6 | 120 |
| Olein fraction of | None | | 16.6 | 26.9 | 130 |
| hardened mixture of soybean oil and palm oil olein having PV 0.0 AV 3.7 M.p. approx. 16° C. | Propyl gallate | 100 | 20.5 | 35.9 | 130 |
| Olein fraction of | None | | 16.4 | 23.2 | 130 |
| hardened rapeseed oil | Propyl gallate | 100 | 23.0 | 35.9 | 130 |
| having | BHA | 100 | 18.2 | 23.4 | 130 |
| PV 0.0 AV 0.6 | | | | | |

TABLE 1-continued

| Oil | Antioxidant | ppm | Measured Oxidograph time, h | Measured Rancimat time, h | Temp. °C. |
|---|---|---|---|---|---|
| M.p. approx. 15° C. "Coatex 01" having PV 0.0 AV 3.7 | None Propyl gallate | 100 | 19.3 22.0 | 29.7 38.5 | 130 130 |
| M.p. approx. 16° C. MCT oil having PV 0.0 AV 0.1 M.p. less than 5° C. | None Propyl gallate TBHQ | 100 100 | 8.0 >48 19.6 | 13.9 >48 24.7 | 130 130 130 |

PV = peroxide value in meq/kg (AOCS Cd 8-53)
AV = anisidine value in anisidine value units (IUPAC 2.504)

TABLE 2

| Oil | Antioxidant | ppm | Calculated Oxidograph time, h | Calculated Rancimat time, h | Temp. °C. |
|---|---|---|---|---|---|
| Soybean oil having | None | | 2.0 | 3.7 | 120 |
| | Propyl gallate | 100 | 3.6 | 7.0 | 120 |
| | BHA | 100 | 2.0 | 3.8 | 120 |
| PV 0.8 | BHT | 100 | 2.2 | 4.0 | 120 |
| AV 3.7 | Ascorbyl palmitate | 200 | 2.1 | 5.2 | 120 |
| M.p. −23 to −20° C. | Mixed natural tocopherols | 200 | 1.9 | 3.8 | 120 |
| Rapeseed oil having | None | | 2.3 | 4.1 | 120 |
| | Propyl gallate | 100 | 4.6 | 7.6 | 120 |
| PV 0.2 | TBHQ | 100 | 4.6 | 9.6 | 120 |
| AV 3.7 | Ascorbyl palmitate | 200 | 2.6 | 6.8 | 120 |
| M.p. −5° C. | Mixed natural tocopherols | 200 | 2.3 | 3.8 | 120 |
| Corn oil having | None | | 3.2 | 6.1 | 120 |
| PV 0.0 | Propyl gallate | 100 | 5.4 | 9.2 | 120 |
| AV 14.1 | TBHQ | 100 | 4.9 | 9.9 | 120 |
| M.p. −18 to −10° C. | Mixed natural tocopherols | 200 | 3.3 | 6.1 | 120 |
| Sunflower oil of a high oleic acid content having | None | | 4.1 | 5.9 | 120 |
| | Propyl gallate | 100 | 5.7 | 8.9 | 120 |
| PV 3.1 | TBHQ | 100 | 6.1 | 10.2 | 120 |
| AV 21.7 | BHA | 100 | 5.9 | 6.7 | 120 |
| M.p. 7° C. | Mixed natural tocopherols | 200 | 5.7 | 8.7 | 120 |
| Double fractionated palm oil having | None | | 7.2 | 12.7 | 120 |
| PV 0.1 | Propyl gallate | 100 | 11.1 | 18.8 | 120 |
| AV 8.7 | TBHQ | 100 | 9.3 | 18.5 | 120 |
| M.p. approx. 16° C. | Mixed natural tocopherols | 200 | 7.4 | 13.6 | 120 |
| Olein fraction of hardened mixture of soybean oil and palm oil olein having PV 0.0 AV 3.7 M.p. approx. 16° C. | None Propyl gallate | 100 | 33.2 41.0 | 53.8 71.8 | 120 120 |
| Olein fraction of hardened rapeseed oil having PV 0.0 AV 0.6 M.p. approx. 15° C. | None Propyl gallate BHA | 100 100 | 32.8 46.0 36.4 | 46.4 71.8 46.8 | 120 120 120 |
| "Coatex 01" having PV 0.0 AV 3.7 M.p. approx. 16° C. | None Propyl gallate | 100 | 38.6 44.0 | 59.4 77.0 | 120 120 |
| MCT oil having PV 0.0 AV 0.1 M.p. less than 5° C. | None Propyl gallate TBHQ | 100 100 | 16.0 >96 39.2 | 27.8 >96 49.4 | 120 120 120 |

PV = peroxide value in meq/kg (AOCS Cd 8-53)
AV = anisidine value in anisidine value units (IUPAC 2.504)

In connection with glyceride oils presence of water and a suitable catalyst may cause hydrolysis with separation of fatty acids from the glycerides. Generally, the fatty acid separation does not involve any consequences in terms of taste, except that glycerides containing short chain fatty acids (having 4–12 carbon atoms) may cause so-called soap taste (e.g. coconut oil, palm kernel oil, babassu oil and synthetically produced MCT oils).

The hydrolysis reaction increases with increasing temperature, but it also takes place at room temperature, even in solid fats. It is known e.g. from Bent Andersen and Turi Roslund: "Low Temperature Hydrolysis of Triglycerides", Proceedings from 14th Scandinavian Symposium on Lipids, June 1987, page 145, that addition of small amounts of soy lecithin (0.65–650 micromoles per kg of product) to solid fats at room temperature reduces or prevents the hydrolysis. Sorbitan monostearate is reported to have the same hydrolysis inhibiting effect (Niiya, I. et al., Sukagaku Vol. 19 (1970), pages 473–181).

The wax in the composition of the invention may be the previously stated natural (animal as well as vegetable) and synthetic waxes. The liquid wax is preferably jojoba oil or a synthetic analog thereof or a vegetable or synthetic long chain ester having physico-chemical properties corresponding to those of jojoba oil or a mixture of such liquid waxes. The solid wax is preferably selected from beeswax, wool wax (lanolin), spermaceti, carnauba wax, candelilla wax, shellak, hardened jojoba oil and synthetic wax. Beeswax has traditionally been accepted and used in the food industry as well as in cosmetics and pharmacy. Beeswax, preferably, a bleached grade (cera alba) or a low-melting candelilla grade is preferred for use in the composition of the invention, but also a low-melting grade of carnauba wax or a synthetic microcrystalline wax type (ozokerite or ceresine) is suitable, in particular when the composition is to be used as a petrolatum. A relatively hard wax type is preferred when the composition is used under warm climatic conditions. The decisive thing is that the wax in coaction with the other components in the composition of the invention contributes to the microcrystalline or amorphous structure and antisticking effect of the composition.

Jojoba oil or a synthetic analog is preferably used together with one of the above-mentioned solid waxes. Preferred amounts are:

| | |
|---|---|
| solid wax | 1–15% |
| liquid wax | 5–50%. |

Furthermore, it is also possible to some extent to regulate the consistency of the composition of the invention having the same content of wax and structuring fat by the selection of a harder wax type, e.g. beeswax or a softer wax type, e.g. the liquid jojoba oil.

The structuring fat used in the composition of the invention is of the type which is previously known for other applications, and which typically consists of hardened and/or high-melting fats or fractions thereof solid at room temperature. Useful structuring fats are e.g. optionally interesterified high-melting fats or fat fractions and optionally interesterified hardened oils, fats or fat fractions and mixtures thereof. Usually, the structuring fat will be characterized by a solid content, determined by the pulse NMR technique described below, at 30° C., of more than 50%, better more than 60% and even better more than 70% and best more than 80%.

By a so-called pulse NMR technique (nuclear magnetic resonance) it is possible to determine the proportion between the protons distributed in the solid and liquid phases of the fat at a given temperature. For example, the solid content of a fat can be plotted as a function of the temperature in the form of the "solid phase profile" of the fat. Equipment useful for solid measurements on fats is e.g. the apparatus "Minispec PC-120 s" from Bruker, Analytische Messtechnik GmbH, Reinstetten-Forshheim, Germany).

Various methods have been developed for determining the solid content by this technique, the differences being primarily the tempering to which a given fat sample is subjected prior to the measurement.

The following method may be used for high-melting glyceride oils: The glyceride oil sample is melted to liquid form in e.g. a microwave oven, following which the oil is distributed in a plurality of measuring glasses. The oil filled measuring glasses are left at 100° C. for one hour and are moved to ice/water bath at 0° C. for 0.5 hour. Following this tempering the measuring glasses are placed in water baths at 10°, 20°, 30°, and 40° C., respectively, for 0.5 hour followed by measurement in the calibrated pulse NMR apparatus (with three pulses per two seconds and an apparatus factor of 1.70 at all the stated temperatures). The measurement results of solid phase are expressed in %.

The following method is used in the examples for the composition of the invention: The sample is melted as above and distributed in a plurality of measuring glasses. The measuring glasses are left at 100° C. for one hour and then placed in ice/water bath at 0° C. for 1.5 hours. Then the measuring glasses are left at 26° C. for 48 hours and are moved again to ice/water bath at 0° C. for 1.5 hours. Finally, tempering takes place for one hour in water bath at the measuring temperature. Measurements are taken in the calibrated pulse NMR apparatus at temperatures 10°, 15°, 20°, 25°, 30° and 35° C. with 1 pulse per 6 seconds. The apparatus factor is 1.6 up to 30° C. and 1.85 at 35° C.

The composition of the invention may contain various types of additions:

crystallization inhibitors, such as partial glycerides, sorbitan fatty acid esters and lecithin;

hydrolysis inhibitors, such as lecithin and sorbitan monostearate;

food product ingredients, such as carbohydrates and proteins;

additives for food products, such as acidity regulating agents, acids, preservative substances/preservative agents, antioxidants, dyes, emulsifiers, gelating agents, modified starches, stabilizers, flavourings/flavouring agents, potentiators of taste, artificial sweeteners and foam inhibitors;

diet supplements, such as vitamins and minerals;

bioactive substances, such as pharmaceuticals (e.g. antibiotics and analgesics as well as irritation relieving, tranquillizing, stimulating, regenerating, healing, antiseptic astringent and inflammation inhibiting substances), pesticides and insect repelling substances;

cosmetic ingredients, such as emollients, perfume, sun filters, polymers, silicone compounds and substances having a moisture retaining, cleaning, cooling, protecting, caring, UV-protecting or insect repelling effect on skin and/or mucous membranes;

pigments; and solvents, such as alcohols.

The crystallization inhibiting additions in the composition of the invention may e.g. be the above-mentioned partial glycerides, sorbitan fatty acid esters and lecithin. A useful crystallization inhibiting additive is of the type stated as glyceride system A in the fat base according to Danish Patent Application 467/91 and International Patent Application WO 92/16184 (PCT/DK92/00080), available under the trade mark "Cremeol FR-36" from Aarhus Oliefabrik A/S, Denmark.

Addition of antioxidants to the composition of the invention serves to interrupt the free radical reaction which is part of the oxidation process of fats. Antioxidants useful as a stabilizing additive in the composition of the invention include e.g. tocopherols (α-tocopherol E 307, γ-tocopherol E 308, δ-tocopherol E 309), tocopherol containing extracts (E 306), ascorbic acid (E 300) and salts and esters thereof, t-butyl hydroxyanisol (BHA, E 320), t-butyl hydroxytoluene (BHT, E 321), t-butyl hydroquinone (TBHQ), propyl gallate (E 310), octyl gallate (E 311), and dodecyl gallate (E312) and to a minor. degree lecithin (E 322). The antioxidant effect may be enhanced by addition of citric acid (E 330, synergist). The stated E numbers refer to the EC positive list system for designating additives to food products.

Preservative additions to the composition of the invention may be conventional antibiotic substances, in particular antibacterial and antifungal additives approved for use in food products and/or in cosmetics and pharmaceuticals.

The invention will be illustrated more fully by the following working examples:

EXAMPLE 1

The following mixture of the stated components was produced:

96% Glyceride oil
3% Structuring fat
1%. Beeswax

The glyceride oil used is an almost liquid fraction of a hardened mixture of 70% soybean oil and 30% liquid fraction of the palm oil (palm oil olein), characterized by a melting point of about 16° C., an iodine value of 86, a rancimat time (120° C. ) of about 60 hours and an AOM stability of about 250 hours.

The structuring fat used is a mixture of 75% hardened solid fraction of palm oil (hardened palm oil stearin) and 25% fully hardened erucic acid rich rapeseed oil, characterized by a solid content determined by pulse NMR technique of 95–98, 93–96, 85–88 and 58–62 at 10°, 20°, 30° and 40° C., respectively.

The composition of the invention was melted by heating to about 50° C. and sprayed on to pieces of liquorice in a continuous oiling drum. The sprayed amount was about 0.1% by weight of the liquorice amount.

Then the surface treated pieces of liquorice were poured into trays and conditioned at room temperature (about 20° C.) for about 12 hours.

The evaluation of the liquorice pieces was made with the following intervals:

Immediately
After one week
Each month for ten months.

Results of the evaluation:

The pieces of liquorice were very shiny, and when stored the pieces of liquorice remained shiny with a fresh appearance. No tendency to sticking together was observed during storage.

In the production it was found that by surface treatment with the composition of the invention the amount of liquorice pieces stuck together was reduced greatly, resulting in less waste (rework).

No form of disagreeable after-taste was observed during storage.

EXAMPLE 2

The mixture stated in Example 1 was also tested on wine gum. The process parameters were the same as in Example 1.

Here it was found that the surface treated pieces of wine gum stuck together the very next day after the test.

EXAMPLE 3

Then a new mixture of the following composition of the same components as in Example 1 was produced:

94% Glyceride oil
3% Structuring fat
3% Beeswax

The composition of the invention was melted by heating to about 55° C., and sprayed on to pieces of wine gum in a continuous oiling drum. The dosing was about 0.1% by weight of the amount of wine gum. The other process parameters were the same as in Example 1. The products were evaluated currently for about 6 months.

Results of the evaluation:

Practically no wine gum pieces stuck together, nor was any sticking-together observed during storage.

The wine gum pieces had a shiny appearance, and there was no sign of desiccation during storage.

No form of disagreeable after-taste was observed during storage.

EXAMPLE 4

The mixture stated in Example 3 was also used for liquorice pieces. Here too the composition of the invention was melted at about 55° C., and the other process parameters were the same as in Example 1. The products were evaluted currently for about 6 months.

Results of the evaluation:

The liquorice pieces were very shiny and preserved the shiny and fresh appearance for the entire evaluation period.

In the production it was found that by surface treatment with the composition of the invention the amount of liquorice pieces stuck together was reduced greatly, resulting in less waste (rework).

No form of disagreeable after-taste was observed during storage.

It was concluded on the basis of the results in Examples 3 and 4 that this mixture may be used for liquorice products as well as jelly articles, such as e.g. wine gum.

EXAMPLE 5

The following mixture of the components stated in Example 1 was-produced:

92% Glyceride oil
3% Structuring fat
5% Beeswax

The composition of the invention was melted by heating to about 55° C. and sprayed on to pieces of wine gum in a continuous oiling drum. The other process parameters were the same as in Example 1. The samples were evaluated currently for about 6 months.

The result of the evaluation was the same as in Example 3.

EXAMPLE 6

The mixture stated in Example 5 was also used for surface treatment of liquorice pieces. The process parameter were the same as in Example 4. The samples were evaluated currently for about 6 months.

Results of the evaluation:

The samples were not as shiny as those in Example 4. On a 0–6 rating scale Example 4 gets the rating 6, and Example 6 the rating 5. The evaluation result in general was the same as in Example 4.

EXAMPLES 7–15

The following mixtures of the same components as-stated in Example 1 were produced:

| EXAMPLE Component | 7 % | 8 % | 9 % | | |
|---|---|---|---|---|---|
| Glyceride oil | 87 | 82 | 77 | | |
| Structuring fat | 3 | 3 | 3 | | |
| Beeswax | 10 | 15 | 20 | | |

| EXAMPLE Component | 10 % | 11 % | 12 % | 13 % | 14 % | 15 % |
|---|---|---|---|---|---|---|
| Glyceride oil | 92 | 87 | 82 | 77 | 79 | 74 |
| Structuring fat | 3 | 3 | 3 | 3 | 6 | 6 |
| Jojoba oil | 5 | 10 | 15 | 20 | 15 | 20 |

The mixtures were produced in the laboratory. The ingredients were mixed and totally melted and then stirred together. The evaluations were made visually after the agents had been left to stand at 20° C. for 2 days.

Of course, the compositions 7, 8 and 9 with 3% structuring fat and increasing amount of beeswax have a harder consistency with increasing addition. There are no signs of graininess. May conceivably be used for surface treatment of extremely soft articles which stick very much together and therefore need a strong barrier.

The compositions 10–13 with 3% structuring fat and increasing amounts of jojoba oil have fairly the same viscosity and appear to be too liquid for surface treatment use.

The compositions 14 and 15 with 6% structuring fat as well as 15 and 20% jojoba oil, respectively, have a jelly-like consistency and appear to be useful as surface treatment compositions. The anti-sticking effect of a surface treatment composition can be evaluated by a simple sensory evaluation, more particularly by tasting the composition. It is an observed fact that the anti-sticking effect will be good if a thin layer settles on the teeth so that they slide more easily against each other. This sensation of the thin layer is obtained when evaluating products with bees's wax. The sensation is partly absent when evaluating products with jojoba oil. The samples 10–15 have no visible crystals.

EXAMPLES 16–19

The following mixtures were produced:

| | EXAMPLE Component | 16 % | 17 % | 18 % | 19 % |
|---|---|---|---|---|---|
| a | glyceride oil | 80.95 | 80.95 | 85.95 | 90.95 |
| b | candelilla wax | 3 | — | — | — |
| | carnauba wax | — | — | 3 | 3 |
| | cera alba | — | 3 | — | — |
| c | structuring fat | 15 | 15 | 10 | 5 |
| d | "Cremeol FR-36" | 1 | 1 | 1 | 1 |
| | soy lecithin | 0.05 | 0.05 | 0.05 | 0.05 |

The glyceride oil used is a liquid fraction of hardened rapeseed oil, characterized by a saponification number of 187, an iodine value of about 85 and a rancimat time (120° C.) of 46 hours.

The structuring fat used is the same as is stated in Example 1.

"Cremeol FR-36" is a vegetable glyceride mixture containing min. 80% mono-/diglyceride.

The compositions 16–19 were produced by mixing the individual components with heating to a homogenous melt and subsequent cooling to about 25° C.

Solid phase was measured by means of pulse NMR at the temperatures 10°, 15°, 20°, 25°, 30° and 35° C. In FIG. 1 the solid phase of the compositions 16–19 is compared with the solid phase of a commercial petrolatum.

EXAMPLES 20–23

The following mixtures were produced:

| | EXAMPLE Component | 20 % | 21 % | 22 % | 23 % |
|---|---|---|---|---|---|
| a | glyceride oil | 85.95 | 70.00 | 70.00 | 70.00 |
| | jojoba oil | — | 20 | 20 | 17 |
| b | cera alba | — | 5 | — | — |
| | carnauba wax | — | — | — | 3 |
| | ozokerite (mp 73° C.) | 3 | — | — | — |
| c | structuring fat | 10 | 5 | 10 | 10 |
| d | "Cremeol FR-36" | 1 | — | — | — |
| | soy lecithin | 0.05 | — | — | — |

The components used: glyceride oil, structuring fat and "Cremeol FR-36" are the same as are used in Examples 16–19.

The compositions 20–26 were produced in the same manner as the compositions 16–19.

Figure 2:
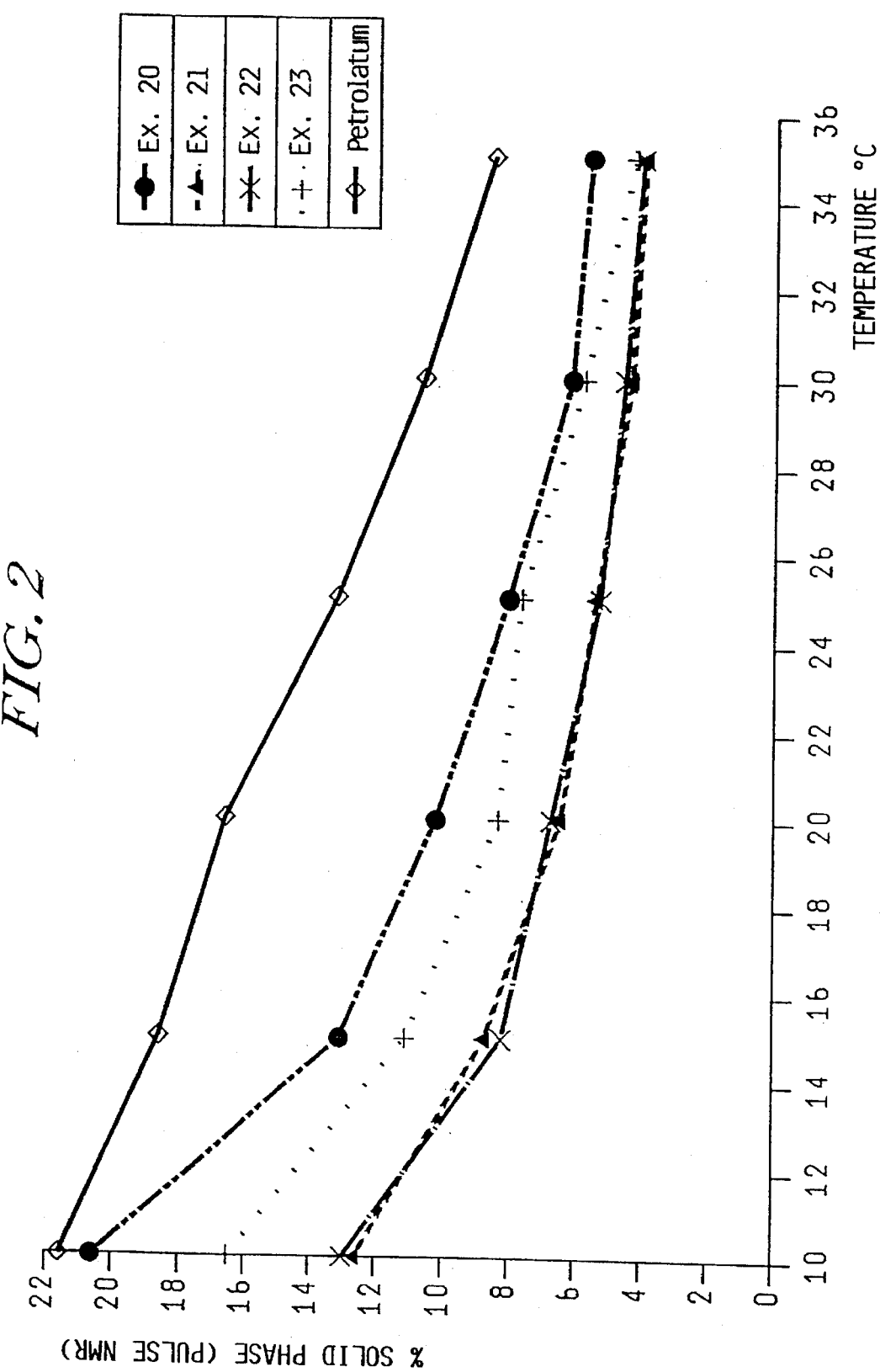

In FIG. 2 the solid phase of the compositions 20–23 is compared with the solid phase of a commercial petrolatum. The solid phase at the various temperatures was measured by means of pulse NMR like in Examples 16–19.

The solid phase curves show that the compositions 20–23 have a softer consistency than the commercial petrolatum and the compositions 16 and 17 in spite of the lower content of wax components of the last-mentioned compositions. Consequently, it is possible—to some extent—to regulate the consistency of the vegetable petrolatum by mixing liquid (jojoba oil) and solid wax components, without any significant change in the concentration of the structuring agent.

The structure of the compositions 20–23 was amorphous—judged visually. Microscope examination reveals scattered, predominantly needle-shaped crystals. The structure can be improved to be more amorphous and plastic by using cooling in a surface-scraped heat exchanger (tube cooling) and plasticizing instead of simple cooling.

Subjectively, the compositions 20–23 were more pleasant to the skin than the petrolatum.

EXAMPLES 24–34

The following mixtures were produced:

| | EXAMPLE Component | 24 % | 25 % | 26 % | 27 % | 28 % | 29 % |
|---|---|---|---|---|---|---|---|
| a | glyceride oil | 50.0 | 50.0 | 50.0 | 50.0 | 30.0 | 30.0 |
| | jojoba oil | 20.0 | 20.0 | 30.0 | 30.0 | 40.0 | 40.0 |
| b | cera alba | 10.0 | — | 10.0 | — | 10.0 | — |
| | candelilla | — | — | — | — | — | — |
| | ozokerite (mp 75° C.) | — | 10.0 | — | 10.0 | — | 10.0 |
| c | Structuring fat | 20.0 | 20.0 | 10.0 | 10.0 | 20.0 | 20.0 |

-continued

| EXAMPLE | | 30 | 31 | 32 | 33 | 34 |
| --- | --- | --- | --- | --- | --- | --- |
| Component | | % | % | % | % | % |
| a | glyceride oil | 60.0 | 60.0 | 55.0 | — | — |
|   | jojoba oil | 20.0 | 20.0 | 30.0 | 81.0 | 81.0 |
| b | cera alba | 10.0 | — | 5.0 | 4.0 | — |
|   | candelilla | — | — | — | — | 4.0 |
|   | ozokerite (mp 73° C.) | — | 10.0 | — | — | — |
| c | structuring fat | 10.0 | 10.0 | 10.0 | 15.0 | 15.0 |

The components used: glyceride oil, structuring fat and "Cremeol FR-36" are the same as are used in Examples 16–19.

The compositions 24–34 were produced in the same manner as the compositions 16–19.

Figure 3:
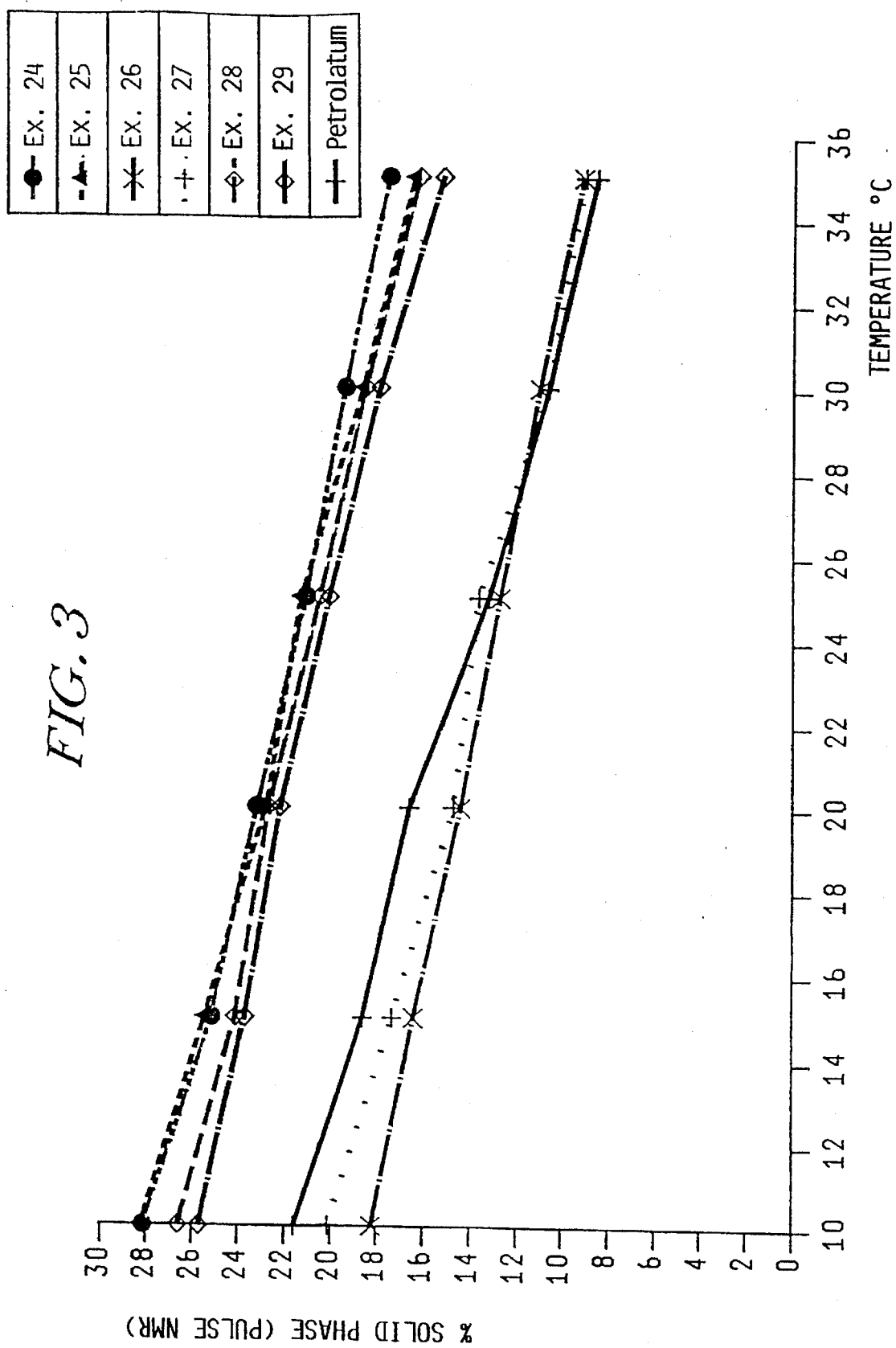
Figure 4:
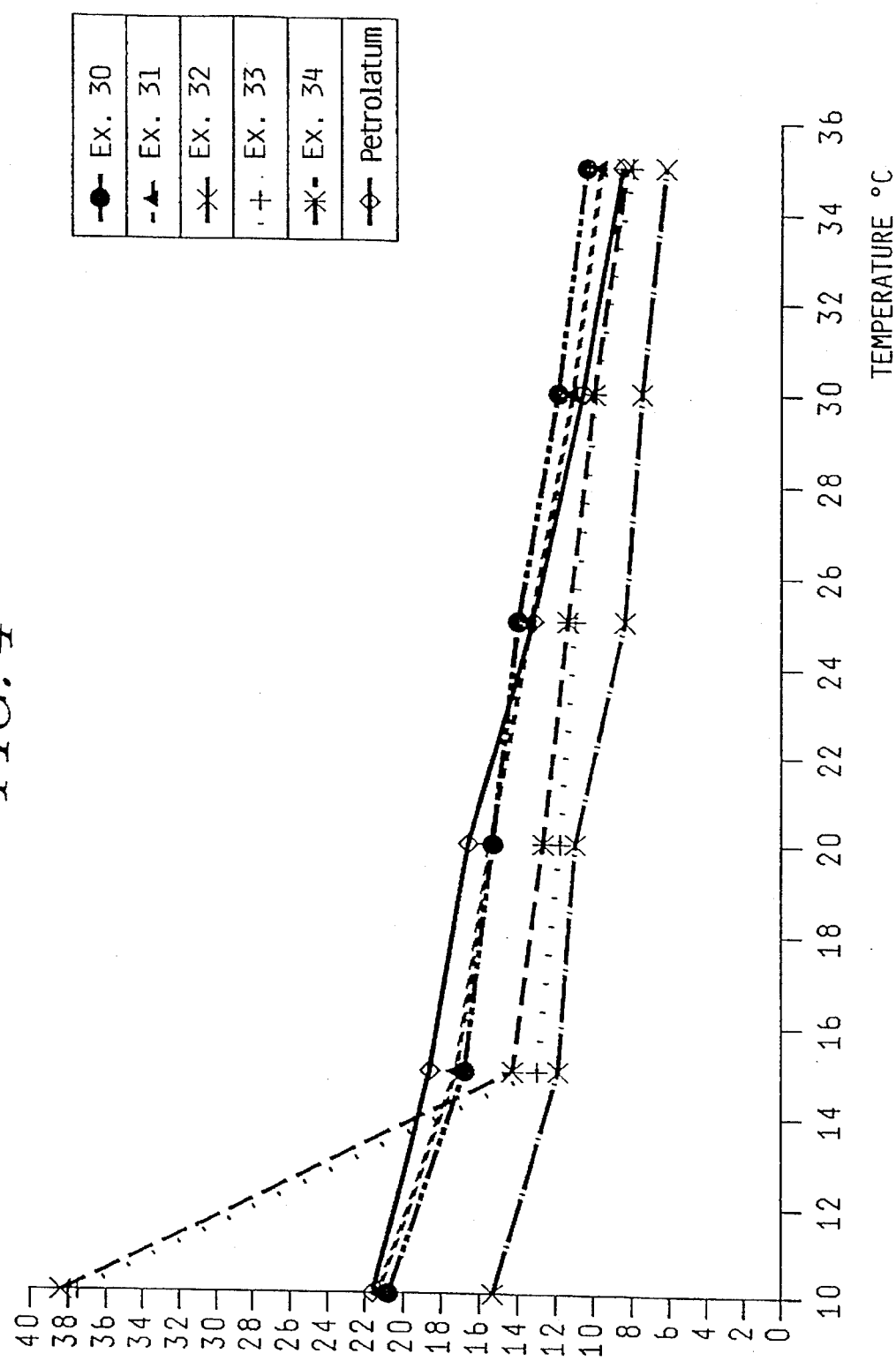

In FIG. 3 the solid phase of the compositions 24–29 and in FIG. 4 the solid phase of the compositions 30–34 are compared with the solid phase of a commercial petrolatum. The solid phase at the various temperatures was measured by means of pulse NMR like in Examples 16–19.

The solid percentages of the compositions 24, 25, 28 and 29 confirm the subjective impression that these have a firmer structure than the petrolatum. Further, these types, when left to stand, tend toward a lower degree of amorphy, accompanied by some thixotropy so that the subjective sensation, when applied to the skin, is initially less pleasant. After-feel is equal to the compositions in Examples 16–23.

The compositions 26, 27, 30 and 31 have structures resembling that of petrolatum. However, these compositions, too, tend toward thixotropy when left to stand so that the compositions, when being applied, have a softer feel and are easier to work. This property represents an advantage cosmetically.

Both subjectively and according to the solid percentages the compositions 32, 33 and 34 are clearly softer than the petrolatum at temperatures above 15° C. If the solid percentages of 30 and 31 are compared, it will be seen that the consistency is determined to some extent by the ratio of liquid to solid wax.

The structure of the compositions 25, 27 and 30–34 is evaluated visually and under microscope to be practically the same as that of the compositions in Examples 20–23; and like these the structure can be improved to be more amorphous by cooling in a surface-scraped heat exchanger (tube cooling) and plasticizing.

EXAMPLE 35

A cleaned fast speed chopper, model SM 45 available from Kramer und Grebe, Germany, was smeared with the composition produced in Example 1 in the form of a thin layer.

Evaluation: After one and two weeks the composition film was intact on the fast speed chopper without any rust attack and without any disagreeable after-taste in the next production charge.

We claim:

1. A composition for surface treatment of confectionery, food products and surfaces which get in contact therewith, and for external treatment of animals and plants, comprising:

(a) a coating component selected from the group consisting of oxidation resistant glyceride oil, liquid wax and mixtures thereof;

(b) solid wax, which may be omitted if (a) comprises liquid wax; and (c) structuring fat; the waxes in the composition consisting essentially of esters of long chain acids and long chain fatty alcohols.

2. The composition of claim 1 which further includes at least one suitable additive, for at least one of surface treatment and ingestion by animals and plants, said suitable additive being selected from the group consisting of crystallization inhibitors, hydrolysis inhibitors, food product ingredients, additives for food products, diet supplements, bioactive substances, cosmetic ingredients, pigments, and solvents.

3. A composition according to claim 2, comprising:

(a) 60–99.9% by weight of said coating component, (b) 0–30% by weight of solid wax, (c) 0.1–20% by weight of structuring fat, (d) 0–20% by weight of said suitable additive.

4. A composition according to claim 3 wherein the oxidation resistant glyceride oil is an oil of vegetable origin selected from the group consisting of (1) at least partly liquid vegetable oils and fractions thereof, (2) at least partly liquid fractions of high-melting vegetable fats, (3) at least partly liquid fractions of hardened, vegetable oils and (4) at least partly liquid fractions of hardened vegetable fats.

5. A composition according to claim 3 characterized in that the oxidation resistant glyceride oil is an at least partly liquid fraction of a hardened animal oil.

6. A composition according to claim 3 wherein the liquid wax is jojoba oil or a synthetic analog thereof or a vegetable or synthetic long chain ester having physico-chemical properties corresponding to those of jojoba oil or a mixture of such liquid waxes.

7. A composition according to claim 3 wherein the solid wax is selected from the group consisting of bees' wax, wool wax (lanolin), spermaceti, carnauba wax, candelilla wax, shellak, and hardened jojoba oil.

8. A composition according to claim 3 wherein the structuring fat is selected from the group consisting of hardened and unhardened fats and fractions thereof which are solid at room temperature.

9. A composition according to claim 3 wherein the structuring fat is Selected from the group consisting of interesterified high-melting fats, interesterified fat fractions, interesterified hardened oils, interesterified hardened fats, interesterified hardened fat fractions, fat fractions and mixtures thereof.

10. A composition according to claim 2 comprising:

(a) 60–99.8% by weight of oxidation resistant glyceride oil, (b) 0.1–30% by weight of solid wax, (c) 0.1–20% by weight of structuring fat, (d) 0–20% by weight of said suitable additive.

11. A composition according to claim 2, comprising:

(a) 70–99.7% by weight of said coating compound, (b) 0–20% by weight Of solid wax, (c) 0.3–20% by weight of structuring fat, (d) 0–10% by weight of said suitable additive.

12. composition according to claim 2, comprising:

(a) 80–99.4% by weight of said coating compound, (b) 0.1–10% by weight, of solid wax, (c) 0.5–6% by weight, of structuring fat, (d) 0–5% by weight of said suitable additive.

13. A composition according to claim 2, comprising:

(a) 60–87% by weight of oxidation resistant glyceride oil and/or liquid wax, (b) 3–10% by weight of solid wax, (c) 10–20% by weight of structuring fat, (d) 0–20% by weight of said suitable additive.

14. A composition according to any of claim 13 wherein the oxidation resistant glyceride oil is a synthetic di- or triglyceride of fatty acids having 6–24 carbon atoms or mixtures thereof.

15. A composition according to claim 13 wherein the structuring fat is characterized by a solid content determined by pulse NMR technique of at least 70%, at 30° C.

16. A composition according to claim 2 wherein the oxidation resistant glyceride oil is an oil of vegetable origin selected from the group consisting of (1) at least partly liquid vegetable oils and fractions thereof, (2) at least partly liquid fractions of high-melting vegetable fats, (3) at least partly liquid fractions of hardened, vegetable oils and (4) at least partly liquid fractions of hardened vegetable fats.

17. A composition according to claim 2 characterized in that the oxidation resistant glyceride oil is an at least partly liquid fraction of a hardened animal oil.

18. A composition according to any of claim 2 wherein the oxidation resistant glyceride oil is a synthetic di- or triglyceride of fatty acids having 6–24 carbon atoms or mixtures thereof.

19. A composition according to claim 2 wherein the liquid wax is jojoba oil or a synthetic analog thereof or a vegetable or synthetic long chain ester having physico-chemical properties corresponding to those of jojoba oil or a mixture of such liquid waxes.

20. A composition according to claim 2 wherein the solid wax is selected from the group consisting of bees' wax, wool wax (lanolin), spermaceti, carnauba wax, candelilla wax, shellak, and hardened jojoba oil.

21. A composition according to claim 2 wherein the structuring fat is selected from the group consisting of hardened and unhardened fats and fractions thereof which are solid at room temperature.

22. A composition according to claim 2 wherein the structuring fat is selected from the group consisting of interesterified high-melting fats, interesterified fat fractions, interesterified hardened oils, interesterified hardened fats, interesterified hardened fat fractions, fat fractions and mixtures thereof.

23. A composition according to claim 2 wherein the structuring fat is characterized by a solid content determined by pulse NMR technique of at least 70%, at 30° C.

24. A composition according to claim 1 wherein the oxidation resistant glyceride oil is an oil of vegetable origin selected from the group consisting of (1) at least partly liquid vegetable oils and fractions thereof, (2) at least partly liquid fractions of high-melting vegetable fats, (3) at least partly liquid fractions of hardened, vegetable oils and (4) at least partly liquid fractions of hardened vegetable fats.

25. A composition according to claim 24 wherein the oxidation resistant glyceride oil is produced from vegetable oils recovered from plants belonging to at least one of the plants of the Palmae family and plants of the genera Garcinia, Pentadesma, Glycine, Carthamus, Olea, Brassica, Helianthus, Zea, Gossypium, Oryza, Shorea, Butyrospermum, Sesamum, Passiflora, Camelina, Limnanthes, Prunus, Triticum, Vitis, Arachis, Corylus, Persea, Madhuca, Juglans, Moringa, Macadamia, Papaver, Carica, Crambe, Adenanthera, Thevetia, Trigonella, Guisotia, Pinus, Hevea, Ricinodendron, Jatropha, Tamarindus, Theobroma, Simarouba, Oenothera, Borago, Cassinia, Flaveria, Stirlingia, Isotropis, Cuphea, Aleurites, Allanblackia, Trichodesma, Phyllanthus, Vaterica, Melia, Alphictonia, Atalaya, Stylidium, Cyperus, Calophyllum, Aloe, Medicago, Mangifera, Curupira, Pongamia, Azadirachta, Myristica, Canarium, Ricinus, Cucurbita, Sapium, Cannabis, Ceiba, Bombax, Linum, Licania, Thea, Camellia, Vernonia and Virula.

26. A composition according to claim 24 wherein the at least partly liquid vegetable oil is recovered from soy, rape, sunflower, corn, cotton seed, grape kernel, thistle, sesame, groundnut or high-oleic acid containing hybrids of rape, sunflower, soy, thistle, groundnut or palm.

27. A composition according to claim 1 characterized in that the oxidation resistant glyceride oil is an at least partly liquid fraction of a hardened animal oil.

28. A composition according to any of claim 1 wherein the oxidation resistant glyceride oil is a synthetic di- or triglyceride of fatty acids having 6–24 carbon atoms or mixtures thereof.

29. A composition according to claim 1 wherein the liquid wax is jojoba oil or a synthetic analog thereof, or a vegetable or synthetic long chain ester having physico-chemical properties corresponding to those of jojoba oil or a mixture of such liquid waxes.

30. A composition according to claim 1 wherein the solid wax is selected from the group consisting of bees wax, wool wax (lanolin), spermaceti, carnauba wax, candelilla wax, shellak, and hardened jojoba oil.

31. A composition according to claim 1 wherein the structuring fat is selected from the group consisting of hardened and unhardened fats and fractions thereof which are solid at room temperature.

32. A composition according to claim 1 wherein the structuring fat is selected from the group consisting of interesterified high-melting fats, interesterified fat fractions, interesterified hardened oils, interesterified hardened fats, interesterified hardened fat fractions, fat fractions and mixtures thereof.

33. A composition according to claim 1 wherein the structuring fat is characterized by a solid content determined by pulse NMR technique of at least 50%, at 30° C.

34. A composition according to claim 1 wherein the structuring fat is characterized by a solid content determined by pulse NMR technique of at least 70%, at 30° C.

* * * * *

UNITED STATES PATENT AND TRADEMARK OFFICE
CERTIFICATE OF CORRECTION

PATENT NO. : 5,660,865

DATED : August 26, 1997

INVENTOR(S) : Arne Pedersen and Frank Johannsen

It is certified that error appears in the above-identified patent and that said Letters Patent is hereby corrected as shown below:

Cover page, item [30], Foreign Application Priority Data, priority date "September 24, 1993" should read "September 25, 1992".

Signed and Sealed this

Ninth Day of December, 1997

Attest:

BRUCE LEHMAN

Attesting Officer

Commissioner of Patents and Trademarks